(12) United States Patent
Li et al.

(10) Patent No.: US 11,680,251 B2
(45) Date of Patent: *Jun. 20, 2023

(54) METHOD FOR ASSEMBLING PRENYL GROUPS ONTO CYCLIC DIPEPTIDES

(71) Applicant: OCEAN UNIVERSITY OF CHINA, Shandong (CN)

(72) Inventors: Wenli Li, Shandong (CN); Tingting Yao, Shandong (CN); Jing Liu, Shandong (CN); Huayue Li, Shandong (CN); Tong Li, Shandong (CN)

(73) Assignee: OCEAN UNIVERSITY OF CHINA, Shandong (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/589,494

(22) Filed: Jan. 31, 2022

(65) Prior Publication Data

US 2022/0154152 A1 May 19, 2022

Related U.S. Application Data

(63) Continuation of application No. 17/042,942, filed as application No. PCT/CN2019/097372 on Jul. 23, 2019, now Pat. No. 11,279,918.

(30) Foreign Application Priority Data

Jul. 26, 2018 (CN) .......................... 201810831718.3

(51) Int. Cl.
*C12N 9/10* (2006.01)
(52) U.S. Cl.
CPC .......... *C12N 9/1085* (2013.01); *C12Y 205/01* (2013.01)

(58) Field of Classification Search
None
See application file for complete search history.

(56) References Cited

U.S. PATENT DOCUMENTS 11,279,918 B2 * 3/2022 Li .......................... C12N 9/1085

FOREIGN PATENT DOCUMENTS

WO WO-2012152923 A1 * 11/2012 ............. C12N 11/16

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Huang et al. Chem Biol. Dec. 17, 2015;22(12):1633-42 (Year: 2015).*
Accession A0A1I1SD39. Nov. 22, 2017 (Year: 2017).*

* cited by examiner

*Primary Examiner* — Christian L Fronda

(57) ABSTRACT

A novel PSL family prenyltransferase has relaxed substrate specificity, which can use a variety of cyclic dipeptides and prenyl donors as substrates to produce various terpenylated diketopiperazines. An amino acid sequence of the prenyltransferase is SEQ ID NO: 1. An application of the prenyltransferase is transferring different prenyl groups to Trp-containing cyclic dipeptides. The prenyltransferase catalyzes the formation of terpenylated diketopiperazines by assembling prenyl groups onto cyclic dipeptides, which provides a new strategy for drug development of diketopiperazines.

3 Claims, 8 Drawing Sheets

Specification includes a Sequence Listing.

METHOD FOR ASSEMBLING PRENYL GROUPS ONTO CYCLIC DIPEPTIDES

CROSS REFERENCE OF RELATED APPLICATION

This is a continuation application of U.S. patent application Ser. No. 17/042,942, filed on Sep. 29, 2020; and claims the priority of Chinese Patent Application CN 201810831718.3, filed to the China National Intellectual Property Administration (CNIPA) on Jul. 26, 2018, the entire content of which are incorporated hereby by reference.

BACKGROUND OF THE PRESENT INVENTION

Field of Invention

The present invention relates to a technical field of genetic engineering and biopharmaceuticals, and more particularly to a novel phytoene-synthase-like (PSL) family prenyltransferase and its applications.

Description of Related Arts

Prenylated secondary metabolites are widely distributed in bacteria, fungi and plants, such as indole alkaloids, flavonoids, and quinones. The introduction of prenyl moieties not only greatly enriches the structural diversities of natural products, but also increases the biological activities of these compounds by enhancing their affinity for membranes as well as the interactions with cellular targets. The studies of structure-activity relationships have shown that the biological activities of prenylated aromatic compounds is generated from the prenyl substitutions. Due to the structure diversities of prenylated natural products, it is difficult to synthesize them via chemical methods. The use of prenyltransferases with substrate promiscuities as tool enzymes provides new strategies to generate novel prenylated derivatives in drug discovery applications.

Aromatic prenyltransferases catalyze the transfer reactions of prenyl moieties from different prenyl donors, e.g. dimethylallyl (DMAPP), geranyl (GPP), farnesyl (FPP), or geranylgeranyl (GGPP) diphosphate, to various aromatic acceptors to form active molecules with multiple biological functions in the biosynthesis of both primary and secondary metabolism of living organisms. The phytoene-synthase-like (PSL) family prenyltransferases are newly discovered, which use aromatic compounds as substrates. Phylogenetic analysis shows that they form the same branch with phytoene synthases instead of typical aromatic prenyltransferases. The only PSL family prenyltransferase reported so far is NzsG involved in the biosynthesis of neocarazostatin from *Streptomyces* sp. MA37, which has strong substrate specificity for both the prenyl donor as well as the prenyl acceptor and can only transfer dimethylallyl pyrophosphate (DMAPP) to precarazostatin.

SUMMARY OF THE PRESENT INVENTION

An object of the present invention is to provide a novel phytoene-synthase-like (PSL) family prenyltransferase with relaxed substrate specificity, which can use a variety of cyclic dipeptides and prenyl donors as substrates to produce terpenylated diketopiperazines.

Firstly, the present invention provides a prenyltransferase, comprising:
a) a protein whose amino acid sequence is SEQ ID NO:1; and
b) a protein, which has prenyl transfer activity of a), obtained by deleting, substituting, inserting or adding one or more of amino acids in a).

A gene encoding the above prenyltransferase is provided, a nucleotide sequence of the gene is SEQ ID NO:2.

The present also provides a recombinant plasmid carrying the above gene.

An application of the prenyltransferase of the present invention is in transferring prenyl donors to cyclic dipeptides.

The prenyl donors are dimethylallyl pyrophosphate (DMAPP), geranyl pyrophosphate (GPP), farnesyl pyrophosphate (FPP) and geranylgeranyl pyrophosphate (GGPP).

The cyclic dipeptides are cyclo (L-Trp-L-Xaa), wherein Xaa is Val, Pro, Leu, Ile, Ala, Thr, Gln, Phe or Tyr.

The prenyltransferase of the present invention produces terpenylated diketopiperazines by assembling prenyl groups onto cyclic dipeptides, which provides new tool enzyme for combinatorial biosynthesis of prenylated diketopiperazines (DKPs) which are meaningful for new drug research and development.

DETAILED DESCRIPTION OF THE PREFERRED EMBODIMENT

Figure 1:
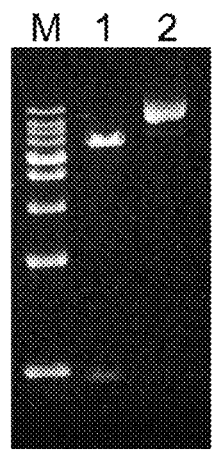
FIG. 1 is a construction verification of a recombinant plasmid of the present invention.
Figure 2:
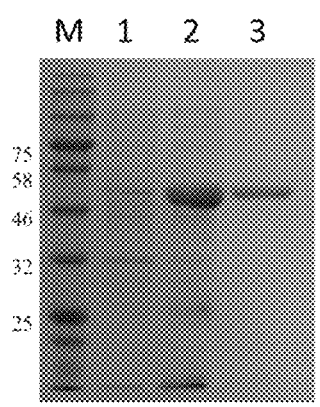
FIG. 2 is a SDS-PAGE analysis of purified DmtC1 of the present invention.

Referring to the drawings, the present invention will be further illustrated.

Embodiment 1: Gene Clone of Isopentenyl Transferase

1. Extraction of Genomic DNA

*Streptomyces youssoufiensis* OUC6819 was cultured in liquid TSBY medium (3% tryptic soya both, 10.3% sucrose, 0.1% tryptone, 0.05% yeast extract) at 30° C. for genomic DNA extraction. Cells were harvested by centrifugation (1 min, 17000×g), and washed (1 mL of STE buffer). 500 μL of lysis solution (3-5 mg/mL lysozyme in STE buffer) was added and incubated at 37° C. until cells became translucent; 250 µL of 6% SDS was then added with further incubation at 37° C. until cells became clear; after addition of ten percent 3 M NaAc (pH 4.8) and 200 µL of a mixture of phenol: chloroform: isoamyl alcohol (25:24:1; v/v/v), the sample was rotated end-over-end for 10 min; after centrifugation (5 min, 17000×g), the aqueous phase was transferred with wide bore pipet into a clean tube. DNA was precipitated by equal volume of isopropanol and spooled using a sealed Pasteur pipet before being transferred into a microcentrifuge tube and rinsed with 70% ethanol. The air-dried DNA was dissolved in a minimal volume of TE buffer for subsequent use.

2. Construction of the Recombinant Plasmid pET32a-dmtC1

A primer pair was designed: P1: 5'-CCGGAATTCACCCGCCAGGAAATGGACG-3'/P2: 5'-CCGCTCGAGCGTCGAGTCGGCGGTCAGGG-3'. The gene dmtC1 was amplified by polymerase chain reaction (PCR) using primer pair P1/P2 from genomes of S. youssoufiensis OUC6819. Genomic DNA was diluted by 10 times as a template for PCR.

PCR Reaction System:

Primer pair P1 and P2 5 µL (50 pmol) each, template 5 µL, 10×Reaction Buffer 10 µL, 2.5 mM dNTP 10 µL, 25 mM $MgCl_2$ 6 µL, pfu DNA Polymerase 1 µL (5 U/µL), adding $ddH_2O$ to 100 µL.

PCR Steps:

Each cycle of PCR includes steps for template denaturation, primer annealing and primer extension. The initial step denatures the genomic DNA by heating it to 98° C. for 10 s. In the next step of a cycle, the temperature is reduced to 66.3° C. for 15 s. Finally, the synthesis of new DNA begins as the reaction temperature is raised to 72° C. for 10 s. After 28 cycles, the amplified product was digested with EcoRI and XhoI, and ligated into pET32a resulting in pET32a-dmtC1 which transforming into *Escherichia coli* DH5a. Positive clones were screening by using enzyme digestion. Results are shown in FIG. 1 (panel iii), wherein target fragment with expected size was obtained. The verified clone was sequenced, wherein a nucleotide sequence of the gene is SEQ ID NO: 2, and an amino acid sequence of the encoded protein is SEQ ID NO: 1.

3. Expression and Purification of DmtC1 in *Escherichia coli*

10 mL overnight culture of *E. coli* BL21 (DE3) harboring DmtC1 expression plasmid was inoculated into 1 L of LB medium (containing 50 µg $mL^{-1}$ ampicillin) and grown at 37° C. with shaking. Expression was induced at an OD600 of approximately 0.6 by addition of IPTG (0.05 mM final concentration), and cultivation was continued for additional 16 hrs at 16° C. The cells were pelleted by centrifugation (15 min at 8000×g) and resuspended in 30 mL of binding buffer A (0.05 M Tris-HCl, 0.5 M NaCl, pH 7.5, containing cOmplete™ protease inhibitor cocktail). The resuspended cells were lysed by sonication in an ice-water bath with an ultrasonic processors VCX750 (Sonics and Materials Inc, Pa., USA), and centrifuged at 10,000×g for 30 min at 4° C. The supernatant was applied to a HisTrap HP column (1 mL, GE Healthcare) and the His-tagged DmtC1 protein was eluted with a linear gradient of imidazole (30-500 mM) in the binding buffer using an ÄKTA Purifier system. After SDS-PAGE analysis, fractions containing pure DmtC1 were pooled, concentrated and exchanged to Tris buffer (0.025 M Tris-HCl, 0.02 M NaCl, and 10.0% glycerol, pH 7.5) by using Amicon Ultra-15 30-kDa cutoff centrifugal concentrator (Millipore) and stored at −80 for subsequent use.

Embodiment 2: In Vitro Assay of DmtC1

The enzymatic assay of DmtC1 was carried out in 50 mM Tris-HCl buffer (pH 8.0) with 2.5 mM $MgCl_2$, containing 10 µM DmtC1, 1 mM DKP, and 0.2 mM FPP. The optimal assay conditions were obtained at 30° C. After 1 hr, the reaction was quenched by the addition of equal volume of methanol and mixed by vortexing. The mixture was centrifuged at 17,000×g for 20 min to remove protein.

Figure 3:
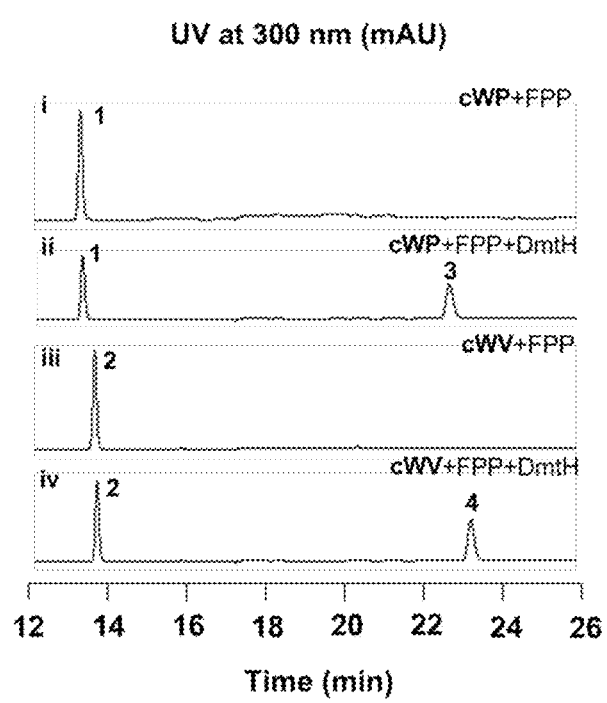
FIG. 3 is a high-performance liquid chromatography (HPLC) traces of DmtC1-catalyzed reactions using different cyclic dipeptide substrates according to the present invention.

The supernatant was then subjected to HPLC analysis using a YMC-Pack ODS-AQ C18 column (150 mm×4.6 mm, particle size of 5 µm, pore size of 120 Å) under the program: phase A consisting of 0.1% (v/v) formic acid and $ddH_2O$, phase B consisting of 0.1% (v/v) formic acid and acetonitrile; 10% B (0-5 min), 10% to 50% B (5-15 min), 80% to 100% B (15-25 min), at a flow rate of 1 mL $min^{-1}$ and UV detection at 300 nm. As shown FIG. 3, a new absorption peak appeared after the reaction, indicating that the enzymatic reaction occurred.

Figure 4:
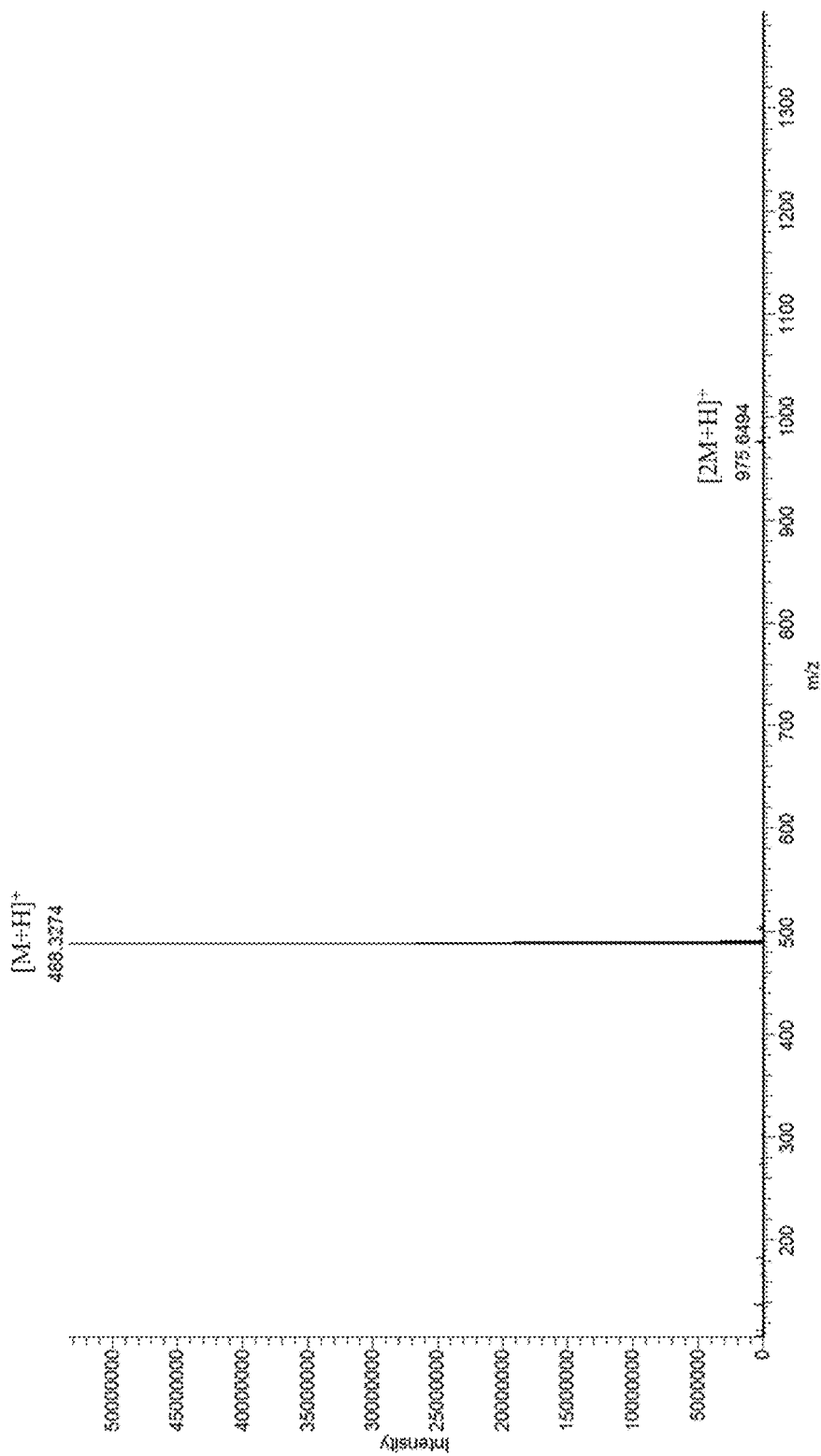
FIG. 4 is a high-resolution mass spectrum (HR-MS) of pre-DMT C according to the present invention.
Figure 5:
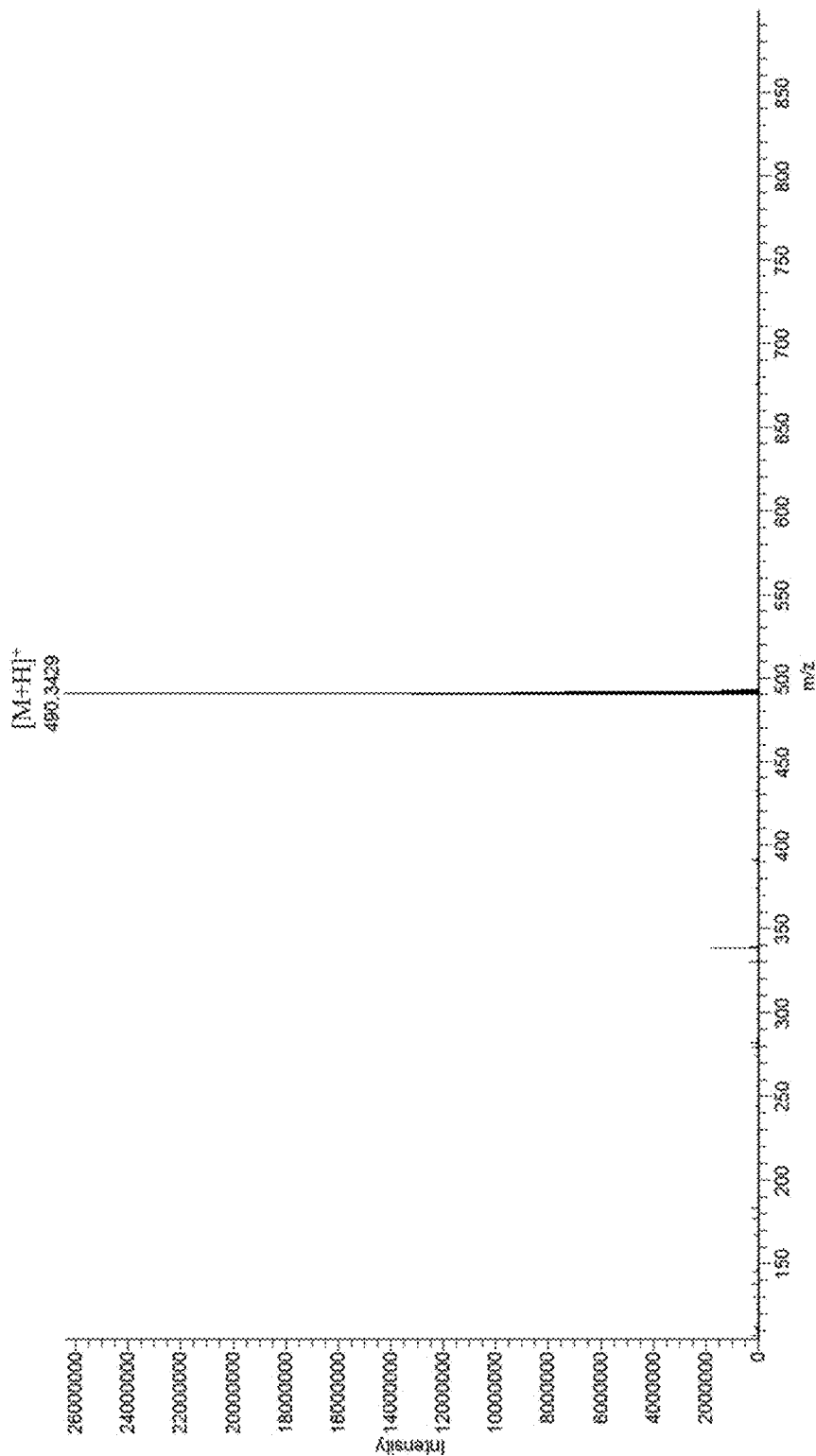
FIG. 5 is a high-resolution mass spectrum (HR-MS) of pre-DMT G according to the present invention.

The obtained product was subjected to high resolution mass spectrometry (HR-MS) analysis (FIGS. 4-5). From the MS spectrum (FIG. 4), $[M+H]^+$ of compound 3 in panel ii is 488.3274, which is consistent with molecular weight of pre-DMT C ($[M+H]^+$ calcd 488.3232); $[M+H]^+$ of compound 4 in panel iv is 490.3429, which is consistent with molecular weight of pre-DMT G ($[M+H]^+$ calcd 490.3389) (FIG. 5).

Embodiment 3: Probing Substrate Promiscuity of DmtC1

Figure 6:
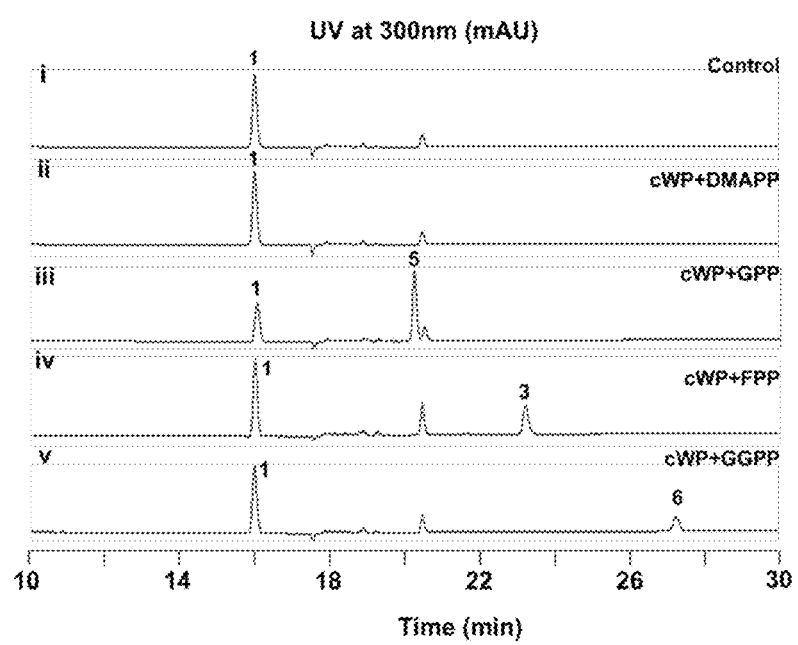
FIG. 6 is a high-performance liquid chromatography (HPLC) traces of DmtC1-catalyzed reactions using different prenyl donors according to the present invention.
Figure 7:
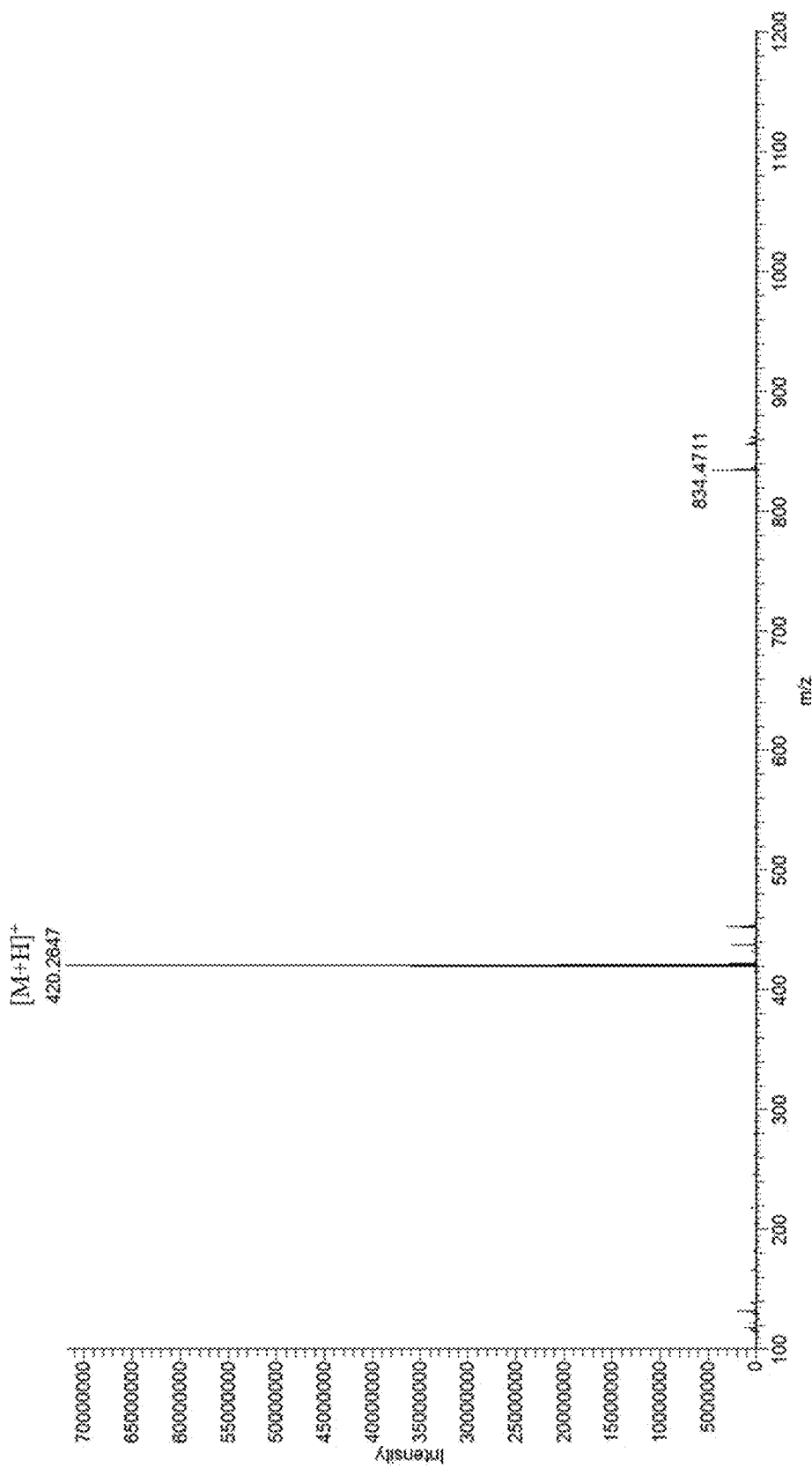
FIG. 7 is a high-resolution mass spectrum (HR-MS) of cWP-GPP according to the present invention.
Figure 8:
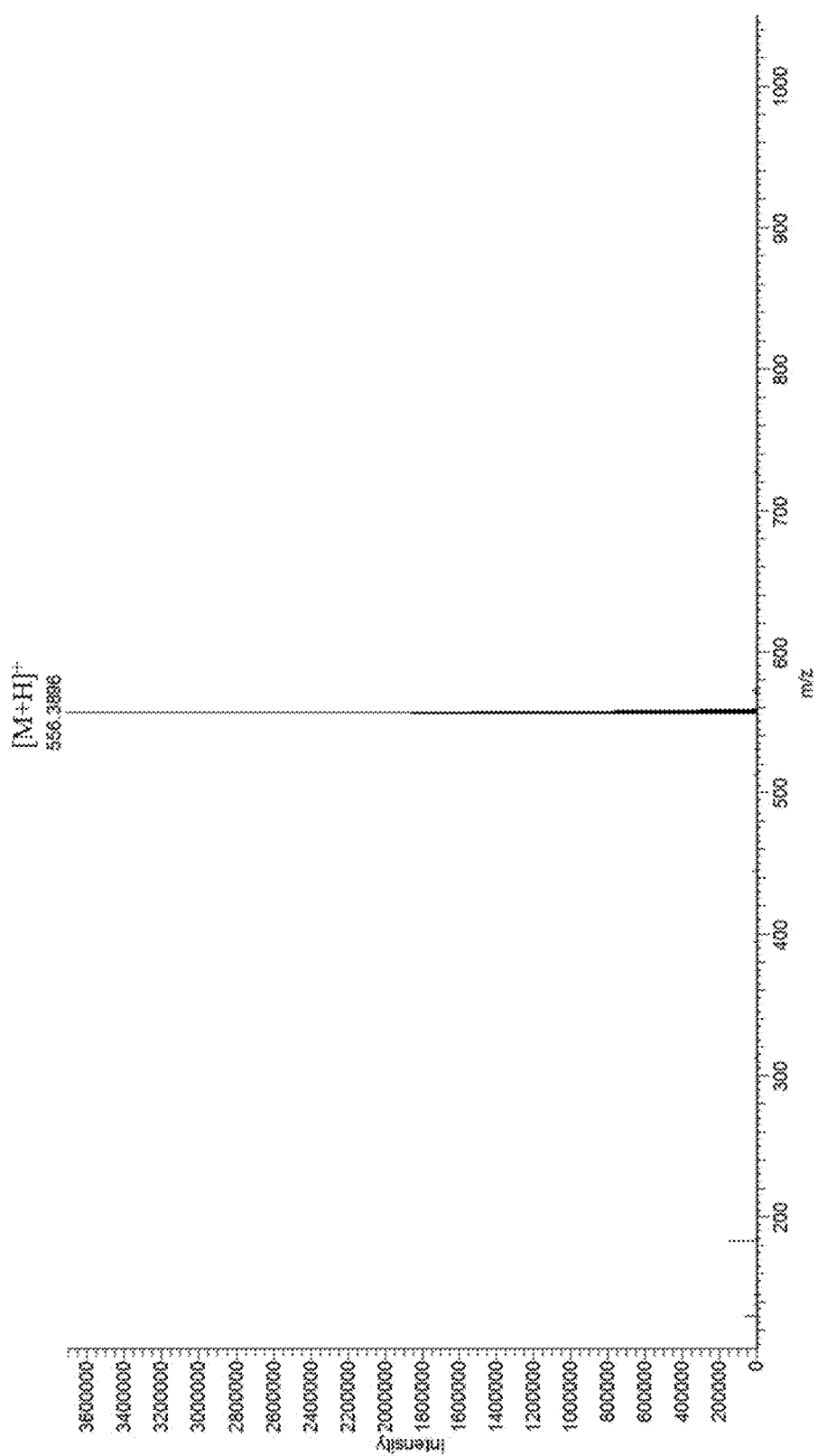
FIG. 8 is a high-resolution mass spectrum (HR-MS) of cWP-GGPP according to the present invention.

When cWP was used as the substrate, the FPP in the enzymatic assay in the embodiment 2 was replaced with DMAPP, GPP or GGPP. HPLC (FIG. 6) and HR-MS analysis (FIGS. 7-8) were performed after the reaction is terminated. $[M+H]^+$ of compound 5 in panel iii is 420.2647, which is consistent with molecular weight of GPP-cWP ($[M+H]^+$ calcd 420.2606) (FIG. 7); $[M+H]^+$ of compound 6 in panel v is 556.3896, which is consistent with molecular weight of GGPP-cWP ($[1\4+H]^+$ calcd 556.3858) (FIG. 8). It is proved that DmtC1 displays broad substrate specificity regarding to the prenyl donors and could be a powerful biocatalytic tool enzyme for combinatorial biosynthesis of terpenylated diketopiperazines.

Embodiment 4: Anti-Vesicular Stomatitis Virus (VSV) Assay of Compound 3 of the Embodiment 2

1. Experimental Samples and Experimental Methods

A sample solution to be tested was compound 3 separated from the embodiment 2. A solution of a required concentration was prepared with DMSO for testing activity.

African green monkey kidney cell line Vero cells were spread on a 96-well plate at 5000/well and cultured in DMEM culture medium for 12 hrs; the vero cells were pretreated with the compound 3 for 1 h with gradient concentrations, and then VSV-GFP viruses were used to infect the cells at M.O.I=0.01 for 1 h; the medium containing compound 3 was then replaced to continue cultivate for 16 hrs; average fluorescence intensity was counted and half inhibition rate ($IC_{50}$) of the compound 3 on VSV was calculated.

2. Experimental Results and Conclusions

Figure 9:
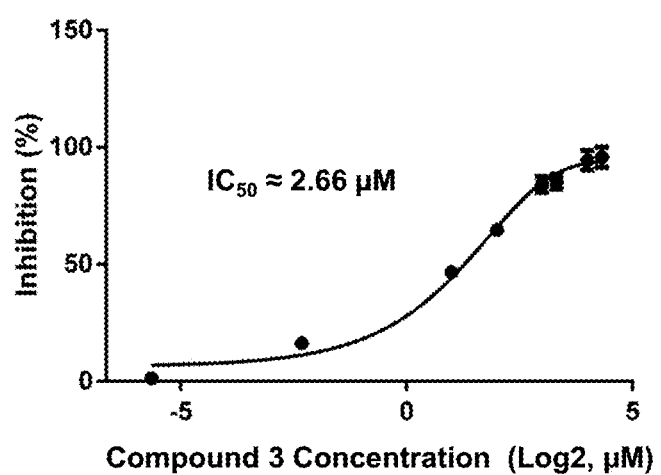
FIG. 9 is a half inhibition rate of pre-DMT C on VSV according to the present invention.

The compound 3 has a significant inhibitory effect on VSV, and $IC_{50}=2.66$ μM (FIG. 9).

INDUSTRIAL APPLICABILITY

In the process of studying the biosynthetic machinery of drimentines in *Streptomyces youssoufiensis* OUC6819, the PSL prenyltransferase DmtC1 with broad substrate specificity was discovered. In vitro biochemical experiments have shown that DmtC1 has a broad spectrum of substrates, and can use a variety of cyclic dipeptides and prenyl donors as the substrates to produce terpenylated diketopiperazines. The relaxed substrate specificity displayed by DmtC1 would enable potential generation of an array of structurally diverse terpenylated diketopiperazines, which are meaningful for new drug research and development.

What is claimed is:

1. A method for assembling prenyl groups onto cyclic dipeptides, comprising steps of:
    encoding a preyltransferase with a recombinant plasmid, wherein the recombinant plasmid comprises a gene encoding the preyltransferase; and
    using the prenyltransferase for assembling the prenyl groups to Trp-containing cyclic dipeptides;
    wherein the prenyltransferase comprises the amino acid sequence of SEQ ID NO:1.

2. The method, as recited in claim 1, wherein the cyclic dipeptides are cyclo (L-Trp-L-Xaa), wherein Xaa is Val, Pro, Leu, Ile, Ala, Thr, Gln, Phe or Tyr.

3. The method, as recited in claim 1, wherein the prenyl groups are dimethylallyl pyrophosphate, geranyl pyrophosphate, farnesyl pyrophosphate or geranylgeranyl pyrophosphate.

* * * * *

SEQUENCE LISTING

```
<160> NUMBER OF SEQ ID NOS: 2

<210> SEQ ID NO 1
<211> LENGTH: 311
<212> TYPE: PRT
<213> ORGANISM: Artificial Sequence
<220> FEATURE:
<223> OTHER INFORMATION: synthesized amino acid sequence

<400> SEQUENCE: 1

Met Thr Arg Gln Glu Met Asp Ala Ala Glu Ile Arg Asp Pro Leu Leu
1               5                   10                  15

Arg Glu Ala Tyr Ala Leu Cys Glu Thr Val Leu Gln Glu Glu Asn His
            20                  25                  30

Ala Ser His Thr Trp Met Arg Asp Gln Leu Arg Pro Asp Arg Arg Pro
        35                  40                  45

Tyr Trp Asp Ala Met Ile Ala Phe Cys Gly His Ala Asp Asp Leu Val
    50                  55                  60

Asp Ala Leu Asn Val Pro Leu Val Glu Arg Leu Arg Arg Tyr Asp Ala
65                  70                  75                  80

Phe Thr Gln Asp Phe Phe Arg Met Leu His Ala Thr Arg Gln Ala Ser
                85                  90                  95

Pro Ala Thr Val Leu Gly Pro Leu Pro Gly Thr Pro Gly Arg Arg Ser
            100                 105                 110

Pro Gly Asp Gly Val Arg Leu Val Ser Leu Ala Phe Cys Asp Phe Val
        115                 120                 125

His Thr Trp Arg Leu Ser Glu Thr Gly Val Arg Gln Ala Gly Gln Ala
    130                 135                 140

Leu Arg Thr Asp Ile Thr Thr Glu Ala Tyr Asp Thr Ala Ser Ala Leu
145                 150                 155                 160

Glu Gln Tyr Met Leu Gly Val Ser Gly Glu Pro Ala Arg Trp Leu Ala
                165                 170                 175

Val Leu Leu Gly Gln Arg Gly Gln Gly Leu Thr Glu Gly Ala Glu Asn
            180                 185                 190

Ala Ala Ile Ser Trp Gly Phe Gly Ile Gln Thr Leu Asp Phe Leu Leu
        195                 200                 205

Asp Ile Glu Glu Asp Leu Arg Leu Gly Lys Leu Tyr Val Pro Leu Asp
    210                 215                 220

Asp Leu Arg Arg Cys Gly Leu Glu Arg Ala Glu Leu Glu Ser Ala Val
225                 230                 235                 240

Ala Ala Arg Gln Pro Ser Gln Pro Leu Arg Asp Val Ile Gly Cys Gln
                245                 250                 255

Leu Asp Arg Val Arg Arg Tyr Phe Thr Ala Ala Glu Gly Trp Leu Asp
            260                 265                 270

Gln Glu Arg Pro Ala Gly Trp Glu Ala Ile Arg Asp Ser Leu Thr Glu
        275                 280                 285

Gly Trp Ala Thr Val Asp Arg Ile Ala Arg Cys Asp His Asp Val Phe
```

```
                290                 295                 300
Ala Leu Thr Ala Asp Ser Thr
305                 310

<210> SEQ ID NO 2
<211> LENGTH: 936
<212> TYPE: DNA
<213> ORGANISM: Artificial Sequence
<220> FEATURE:
<223> OTHER INFORMATION: synthesized nucleotide sequence

<400> SEQUENCE: 2
atgacccgcc aggaaatgga cgcggccgag atccgcgacc cgctcctgcg ggaggcgtac        60
gccctgtgcg agacggtcct ccaggaggag aaccacgcat cccacacctg gatgcgcgac       120
caactccgac ccgaccgacg gccgtactgg gacgccatga tcgccttctg tgggcacgct       180
gacgacctgg tcgacgcgct caacgtgccg ctggtggagc ggctgcgccg ctacgacgcg       240
ttcacccagg acttcttccg catgctgcac gccacgcggc aggccagccc cgccaccgtg       300
ctcggcccgc tgcccggcac gccgggccgc cgctcgcccg gggacggggt gcgcctggtg       360
tcgctggcgt tctgcgactt cgtccacacc tggcggctgt ccgagacggg cgtccgccag       420
gccggtcagg cactgcgcac ggacatcacc accgaggcgt acgacacggc cagcgcgctg       480
gagcagtaca tgctcggtgt cagcggcgaa cccgcgcgct ggctcgccgt cctgctcggc       540
cagcgcgggc agggcctcac cgaggggggcc gagaacgcgg cgatatcctg ggggttcggg       600
atccagacgc tggacttcct gctcgacatc gaggaagacc tgcgcctggg caagctctac       660
gtaccccttg acgacctgcg ccgctgcggc ctggagcgcg ccgagttgga gtcggccgtc       720 gcggccggc agccctcgca gccgttgcgc gacgtgattg gctgtcaact ggatcgggtg       780
cgccggtact tcacggccgc cgaagggtgg ctcgaccagg agcgcccggc gggctgggag       840
gcgatccgcg actcgctcac cgagggctgg gccacggtgg accggatcgc ccgctgcgac       900
cacgacgtct tcgccctgac cgccgactcg acgtaa                                 936
```